United States Patent
Zhu et al.

(10) Patent No.: US 10,376,572 B2
(45) Date of Patent: Aug. 13, 2019

(54) IMMUNOGENIC COMPOSITION FOR PREVENTING PNEUMOCOCCAL DISEASES AND PREPARATION METHOD THEREOF

(71) Applicant: CANSINO BIOLOGICS INC., Tianjin (CN)

(72) Inventors: Tao Zhu, Tianjin (CN); Lei Duan, Tianjin (CN); Mingming Yang, Tianjin (CN); Zhongqi Shao, Tianjin (CN); Xuefeng Yu, Tianjin (CN); Helen Huihua Mao, Tianjin (CN); Dongxu Qiu, Tianjin (CN)

(73) Assignee: CANSINO BIOLOGICS INC., Tianjin (CN)

( * ) Notice: Subject to any disclaimer, the term of this patent is extended or adjusted under 35 U.S.C. 154(b) by 0 days.

(21) Appl. No.: 15/582,400

(22) Filed: Apr. 28, 2017

(65) Prior Publication Data
US 2018/0296660 A1  Oct. 18, 2018

Related U.S. Application Data

(63) Continuation of application No. PCT/CN2015/093056, filed on Oct. 28, 2015.

(30) Foreign Application Priority Data

Oct. 31, 2014 (CN) .......................... 2014 1 0605626

(51) Int. Cl.
| | |
|---|---|
| *A61K 39/00* | (2006.01) |
| *A61K 39/09* | (2006.01) |
| *A61K 39/116* | (2006.01) |
| *A61P 31/04* | (2006.01) |

(52) U.S. Cl.
CPC .... *A61K 39/092* (2013.01); *A61K 39/001164* (2018.08); *A61K 39/116* (2013.01); *A61P 31/04* (2018.01); *A61K 2039/545* (2013.01); *A61K 2039/55505* (2013.01); *A61K 2039/55588* (2013.01)

(58) Field of Classification Search
CPC .................................................... A61K 39/092
See application file for complete search history.

(56) References Cited

U.S. PATENT DOCUMENTS

| | | | | |
|---|---|---|---|---|
| 5,679,768 A | * | 10/1997 | Briles | C07K 14/28 424/190.1 |
| 5,955,089 A | * | 9/1999 | Briles | A61K 39/092 424/165.1 |
| 2011/0002962 A1 | * | 1/2011 | Briles | C07K 14/3156 424/244.1 |

* cited by examiner

*Primary Examiner* — Albert M Navarro

(74) *Attorney, Agent, or Firm* — Flener IP & Business Law; Zareefa B. Flener

(57) ABSTRACT

The invention provides an immunogenic composition for preventing pneumococcal diseases, comprising PspA-MRX1, PspA-EF5668, PspA-EF3296 and PlyL460D, wherein the amount of each component is 10-100 μg/ml; the immunogenic composition is prepared by adding to aluminum adjuvant the corresponding dosages of the four stock solutions PspA-mRX1, PspA-EF5668, PspA-EF3296 and PlyL460D, and mixing them homogeneously; the immunogenic composition can prevent infection and invasion by *Streptococcus pneumonia*, covering more than 95% of the strains in clinic. The immunogenic composition has a wide application in the prevention of pneumonia, and is suitable for large-scale production in industry for its simple preparation method, low production cost, and short production cycle.

7 Claims, 1 Drawing Sheet
Specification includes a Sequence Listing.

SEQUENCE LISTING

<160> NUMBER OF SEQ ID NOS: 4

<210> SEQ ID NO 1
<211> LENGTH: 315
<212> TYPE: PRT
<213> ORGANISM: Escherichia coli

<400> SEQUENCE: 1

```
Met Glu Glu Ser Pro Val Ala Ser Gln Ser Lys Ala Glu Lys Asp Tyr
1               5                   10                  15

Asp Ala Ala Lys Lys Asp Ala Lys Asn Ala Lys Lys Ala Val Glu Asp
                20                  25                  30

Ala Gln Lys Ala Leu Asp Asp Ala Lys Ala Ala Gln Lys Lys Tyr Asp
            35                  40                  45

Glu Asp Gln Lys Lys Thr Glu Glu Lys Ala Ala Leu Glu Lys Ala Ala
        50                  55                  60

Ser Glu Glu Met Asp Lys Ala Val Ala Ala Val Gln Gln Ala Tyr Leu
65                  70                  75                  80

Ala Tyr Gln Gln Ala Thr Asp Lys Ala Ala Lys Asp Ala Ala Asp Lys
                85                  90                  95
```

-continued

```
Ile Ile Asp Glu Ala Lys Lys Arg Glu Glu Ala Lys Thr Lys Phe
                100                 105                 110

Asn Thr Val Arg Ala Met Val Val Pro Glu Pro Glu Gln Leu Ala Glu
            115                 120                 125

Thr Lys Lys Lys Ser Glu Glu Ala Lys Gln Lys Ala Pro Glu Leu Thr
        130                 135                 140

Lys Lys Leu Glu Glu Ala Glu Lys Lys Val Thr Glu Ala Arg Gln Lys
145                 150                 155                 160

Leu Asp Ala Glu Lys Gln Lys Val Asp Ala Glu Val Ala Pro Gln
                165                 170                 175

Ala Lys Ile Ala Glu Leu Glu Asn Gln Val His Arg Leu Glu Gln Glu
            180                 185                 190

Leu Lys Glu Ile Asp Glu Ser Glu Ser Glu Asp Tyr Ala Lys Glu Gly
        195                 200                 205

Phe Arg Ala Pro Leu Gln Ser Lys Leu Asp Ala Lys Lys Ala Lys Leu
    210                 215                 220

Ser Lys Leu Glu Glu Leu Ser Asp Lys Ile Asp Glu Leu Asp Ala Glu
225                 230                 235                 240

Ile Ala Lys Leu Glu Asp Gln Leu Lys Ala Ala Glu Glu Asn Asn Asn
                245                 250                 255

Val Glu Asp Tyr Phe Lys Glu Gly Leu Glu Lys Thr Ile Ala Ala Lys
            260                 265                 270

Lys Ala Glu Leu Glu Lys Thr Glu Ala Asp Leu Lys Lys Ala Val Asn
        275                 280                 285

Glu Pro Glu Lys Pro Ala Pro Ala Pro Glu Thr Pro Ala Pro Glu Ala
    290                 295                 300

Pro Ala Glu Gln Pro Lys Pro Ala Pro Ala Pro
305                 310                 315

<210> SEQ ID NO 2
<211> LENGTH: 370
<212> TYPE: PRT
<213> ORGANISM: Escherichia coli

<400> SEQUENCE: 2

Met Glu Glu Ala Pro Val Ala Asn Gln Ser Lys Ala Glu Lys Asp Tyr
1               5                   10                  15

Asp Ala Ala Val Lys Lys Ser Glu Ala Ala Lys Lys Asp Tyr Glu Thr
                20                  25                  30

Ala Lys Lys Lys Ala Glu Asp Ala Gln Lys Lys Tyr Asp Glu Asp Gln
            35                  40                  45

Lys Lys Thr Glu Ala Lys Ala Glu Lys Glu Arg Lys Ala Ser Glu Lys
        50                  55                  60

Ile Ala Glu Ala Thr Lys Glu Val Gln Gln Ala Tyr Leu Ala Tyr Leu
65                  70                  75                  80

Gln Ala Ser Asn Glu Ser Gln Arg Lys Glu Ala Asp Lys Lys Ile Lys
                85                  90                  95

Glu Ala Thr Gln Arg Lys Asp Glu Ala Glu Ala Phe Ala Thr Ile
            100                 105                 110

Arg Thr Thr Ile Val Val Pro Glu Pro Ser Glu Leu Ala Glu Thr Lys
        115                 120                 125

Lys Lys Ala Glu Glu Ala Thr Lys Glu Ala Glu Val Ala Lys Lys Lys
    130                 135                 140

Ser Glu Glu Ala Ala Lys Glu Val Glu Val Glu Lys Asn Lys Ile Leu
145                 150                 155                 160
```

Glu Gln Asp Ala Glu Asn Glu Lys Lys Ile Asp Val Leu Gln Asn Lys
                165                 170                 175

Val Ala Asp Leu Glu Lys Gly Ile Ala Pro Tyr Gln Asn Glu Val Ala
            180                 185                 190

Glu Leu Asn Lys Glu Ile Ala Arg Leu Gln Ser Asp Leu Lys Asp Ala
        195                 200                 205

Glu Glu Asn Asn Val Glu Asp Tyr Ile Lys Glu Gly Leu Glu Gln Ala
    210                 215                 220

Ile Thr Asn Lys Lys Ala Glu Leu Ala Thr Thr Gln Gln Asn Ile Asp
225                 230                 235                 240

Lys Thr Gln Lys Asp Leu Glu Asp Ala Glu Leu Glu Leu Glu Lys Val
                245                 250                 255

Leu Ala Thr Leu Asp Pro Glu Gly Lys Thr Gln Asp Glu Leu Asp Lys
            260                 265                 270

Glu Ala Ala Glu Ala Glu Leu Asn Glu Lys Val Glu Ala Leu Gln Asn
        275                 280                 285

Gln Val Ala Glu Leu Glu Glu Leu Ser Lys Leu Glu Asp Asn Leu
    290                 295                 300

Lys Asp Ala Glu Thr Asn Asn Val Glu Asp Tyr Ile Lys Glu Gly Leu
305                 310                 315                 320

Glu Glu Ala Ile Ala Thr Lys Lys Ala Glu Leu Glu Lys Thr Gln Lys
                325                 330                 335

Glu Leu Asp Ala Ala Leu Asn Glu Leu Gly Pro Asp Gly Asp Glu Glu
            340                 345                 350

Glu Thr Pro Ala Pro Ala Pro Gln Pro Glu Lys Pro Ala Glu Glu Pro
        355                 360                 365

Glu Asn
    370

<210> SEQ ID NO 3
<211> LENGTH: 479
<212> TYPE: PRT
<213> ORGANISM: Escherichia coli

<400> SEQUENCE: 3

Met Glu Glu Ser Pro Gln Val Val Glu Lys Ser Ser Leu Glu Lys Lys
1               5                   10                  15

Tyr Glu Glu Ala Lys Ala Lys Ala Asp Thr Ala Lys Lys Asp Tyr Glu
            20                  25                  30

Thr Ala Lys Lys Lys Ala Glu Asp Ala Gln Lys Lys Tyr Glu Asp Asp
        35                  40                  45

Gln Lys Arg Thr Glu Glu Lys Ala Arg Lys Glu Ala Glu Ala Ser Gln
    50                  55                  60

Lys Leu Asn Asp Val Ala Leu Val Val Gln Asn Ala Tyr Lys Glu Tyr
65                  70                  75                  80

Arg Glu Val Gln Asn Gln Arg Ser Lys Tyr Lys Ser Asp Ala Glu Tyr
                85                  90                  95

Gln Lys Lys Leu Thr Glu Val Asp Ser Lys Ile Glu Lys Ala Arg Lys
            100                 105                 110

Glu Gln Gln Asp Leu Gln Asn Lys Phe Asn Glu Val Arg Ala Val Val
        115                 120                 125

Val Pro Glu Pro Asn Ala Leu Ala Glu Thr Lys Lys Ala Glu Glu
    130                 135                 140

Ala Lys Ala Glu Glu Lys Val Ala Lys Arg Lys Tyr Asp Tyr Ala Thr

```
            145                 150                 155                 160
    Leu Lys Val Ala Leu Ala Lys Lys Glu Val Glu Ala Lys Glu Leu Glu
                    165                 170                 175
    Ile Glu Lys Leu Gln Tyr Glu Ile Ser Thr Leu Glu Gln Glu Val Ala
                    180                 185                 190
    Thr Ala Gln His Gln Val Asp Asn Leu Lys Lys Leu Leu Ala Gly Ala
                    195                 200                 205
    Asp Pro Asp Asp Gly Thr Glu Val Ile Glu Ala Lys Leu Lys Lys Gly
            210                 215                 220
    Glu Ala Glu Leu Asn Ala Lys Gln Ala Glu Leu Ala Lys Lys Gln Thr
    225                 230                 235                 240
    Glu Leu Glu Lys Leu Leu Asp Ser Leu Asp Pro Glu Gly Lys Thr Gln
                    245                 250                 255
    Asp Glu Leu Asp Lys Glu Ala Glu Glu Ala Leu Asp Lys Lys Ala
                    260                 265                 270
    Asp Glu Leu Gln Asn Lys Val Ala Asp Leu Glu Lys Glu Ile Ser Asn
                    275                 280                 285
    Leu Glu Ile Leu Leu Gly Gly Ala Asp Pro Glu Asp Asp Thr Ala Ala
            290                 295                 300
    Leu Gln Asn Lys Leu Ala Ala Lys Lys Ala Glu Leu Ala Lys Lys Gln
    305                 310                 315                 320
    Thr Glu Leu Glu Lys Leu Leu Asp Ser Leu Asp Pro Glu Gly Lys Thr
                    325                 330                 335
    Gln Asp Glu Leu Asp Lys Glu Ala Glu Ala Glu Leu Asp Lys Lys
                    340                 345                 350
    Ala Asp Glu Leu Gln Asn Lys Val Ala Asp Leu Glu Lys Glu Ile Ser
                    355                 360                 365
    Asn Leu Glu Ile Leu Leu Gly Gly Ala Asp Ser Glu Asp Asp Thr Ala
            370                 375                 380
    Ala Leu Gln Asn Lys Leu Ala Thr Lys Lys Ala Glu Leu Glu Lys Thr
    385                 390                 395                 400
    Gln Lys Glu Leu Asp Ala Ala Leu Asn Glu Leu Gly Pro Asp Gly Asp
                    405                 410                 415
    Glu Glu Glu Thr Pro Ala Pro Ala Pro Gln Pro Glu Gln Pro Ala Pro
                    420                 425                 430
    Ala Pro Lys Pro Glu Gln Pro Ala Pro Lys Pro Glu Gln Pro
                    435                 440                 445
    Ala Pro Ala Pro Lys Pro Glu Gln Pro Ala Pro Lys Pro Glu
            450                 455                 460
    Gln Pro Ala Pro Ala Pro Lys Pro Glu Gln Pro Ala Lys Pro Glu
    465                 470                 475

<210> SEQ ID NO 4
<211> LENGTH: 471
<212> TYPE: PRT
<213> ORGANISM: Escherichia coli

<400> SEQUENCE: 4

Met Ala Asn Lys Ala Val Asn Asp Phe Ile Leu Ala Met Asn Tyr Asp
    1               5                   10                  15
    Lys Lys Lys Leu Leu Thr His Gln Gly Glu Ser Ile Glu Asn Arg Phe
                    20                  25                  30
    Ile Lys Glu Gly Asn Gln Leu Pro Asp Glu Phe Val Val Ile Glu Arg
                    35                  40                  45
```

```
Lys Lys Arg Ser Leu Ser Thr Asn Thr Ser Asp Ile Ser Val Thr Ala
     50                  55                  60
Tyr Asn Asp Ser Arg Leu Tyr Pro Gly Ala Leu Leu Val Val Asp Glu
 65              70                  75                  80
Thr Leu Leu Glu Asn Asn Pro Thr Leu Leu Ala Val Asp Arg Ala Pro
                 85                  90                  95
Met Thr Tyr Ser Ile Asp Leu Pro Gly Leu Ala Ser Ser Asp Ser Phe
                100                 105                 110
Leu Gln Val Glu Asp Pro Ser Asn Ser Ser Val Arg Gly Ala Val Asn
            115                 120                 125
Asp Leu Leu Ala Lys Trp His Gln Asp Tyr Gly Gln Val Asn Asn Val
    130                 135                 140
Pro Ala Arg Met Gln Tyr Glu Lys Ile Thr Ala His Ser Met Glu Gln
145                 150                 155                 160
Leu Lys Val Lys Phe Gly Ser Asp Phe Glu Lys Thr Gly Asn Ser Leu
                165                 170                 175
Asp Ile Asp Phe Asn Ser Val His Ser Gly Glu Lys Gln Ile Gln Ile
                180                 185                 190
Val Asn Phe Lys Gln Ile Tyr Tyr Thr Val Ser Val Asp Ala Val Lys
            195                 200                 205
Asn Pro Gly Asp Val Phe Gln Asp Thr Val Thr Val Glu Asp Leu Lys
    210                 215                 220
Gln Arg Gly Ile Ser Ala Glu Arg Pro Leu Val Tyr Ile Ser Ser Val
225                 230                 235                 240
Ala Tyr Gly Arg Gln Val Tyr Leu Lys Leu Glu Thr Thr Ser Lys Ser
                245                 250                 255
Asp Glu Val Glu Ala Ala Phe Glu Ala Leu Ile Lys Gly Val Lys Val
            260                 265                 270
Ala Pro Gln Thr Glu Trp Lys Gln Ile Leu Asp Asn Thr Glu Val Lys
    275                 280                 285
Ala Val Ile Leu Gly Gly Asp Pro Ser Ser Gly Ala Arg Val Val Thr
290                 295                 300
Gly Lys Val Asp Met Val Glu Asp Leu Ile Gln Glu Gly Ser Arg Phe
305                 310                 315                 320
Thr Ala Asp His Pro Gly Leu Pro Ile Ser Tyr Thr Thr Ser Phe Leu
                325                 330                 335
Arg Asp Asn Val Val Ala Thr Phe Gln Asn Ser Thr Tyr Val Glu
            340                 345                 350
Thr Lys Val Thr Ala Tyr Arg Asn Gly Asp Leu Leu Leu Asp His Ser
            355                 360                 365
Gly Ala Tyr Val Ala Gln Tyr Tyr Ile Thr Trp Asp Glu Leu Ser Tyr
    370                 375                 380
Asp His Gln Gly Lys Glu Val Leu Thr Pro Lys Ala Trp Asp Arg Asn
385                 390                 395                 400
Gly Gln Asp Leu Thr Ala His Phe Thr Thr Ser Ile Pro Leu Lys Gly
                405                 410                 415
Asn Val Arg Asn Leu Ser Val Lys Ile Arg Glu Cys Thr Gly Leu Ala
            420                 425                 430
Trp Glu Trp Trp Arg Thr Val Tyr Glu Lys Thr Asp Leu Pro Leu Val
            435                 440                 445
Arg Lys Arg Thr Ile Ser Ile Trp Gly Thr Thr Asp Tyr Pro Gln Val
    450                 455                 460
```

```
Glu Asp Lys Val Glu Asn Asp
465                 470
```

IMMUNOGENIC COMPOSITION FOR PREVENTING PNEUMOCOCCAL DISEASES AND PREPARATION METHOD THEREOF

CROSS-REFERENCE TO RELATED APPLICATION

The application is a continuation of PCT/CN2015/093056 (WO 2016/066095 A1, filed on Oct. 28, 2015), which claims priority from CN Patent Application Serial No. 201410605626.5 (filed on Oct. 31, 2014), the entire contents of which are incorporated herein by reference for all purposes.

TECHNICAL FIELD

The invention relates to the field of biopharmaceuticals, in particular, immunogenic compositions, vaccine formulations, and kits for preventing pneumococcal diseases, and preparation methods thereof.

BACKGROUND ART

*Streptococcus pneumoniae* (*S. pn*) is one of the most important causes of death around the world, and is an important pathogenic bacterium for invasive and noninvasive infection such as pneumonia, meningitis, and otitis media. *Streptococcus pneumoniae* resides in healthy human, typically colonizing pharynx nasalis, and about 40%-70% of humans carry the bacterium. When the body's immune function weakens, the pathogenic bacterium may spread to the lung and cause pneumonia. Besides the carriage, one can also acquire pneumococcal infection by contacting other persons or patients carrying the bacterium.

Vaccination is an effective and specific preventive means, and has an excellent health-economic value. Currently, the widely applied vaccines for preventing pneumococcal diseases mainly include two classes, i.e., polysaccharide vaccines (23-valent polysaccharide vaccine, suitable for people above 2 years old) and polysaccharide-protein conjugate vaccines (7-valent, 10-valent or 13-valent, suitable for infants under 2 years old).

Pneumococcal polysaccharide vaccine refers to "23-valent pneumococcal polysaccharide vaccine", which can cover 23 serotypes that generally cause about 90% of pneumococcal infection. Most of healthy adults can generate protective antibodies against all or most of *Streptococcus pneumonia* strains 2-3 weeks after vaccination. Since the 23-valent pneumococcal vaccine can effectively prevent pneumonia, it has been used in more than 30 countries and regions, including USA and Canada, for more than 14 years. The vaccine has been shown to have a 92% protective efficacy and a good safety record. The protection can last for at least five years. It is suggested that children at the age of 2 or older with poor immunity or with recurrent pneumonia as well as the high risk population (such as children with asplenia) should be immunized with the vaccine.

The capsular polysaccharide antigens comprised in 23-valent pneumococcal polysaccharide vaccine are T cell independent antigens, which can stimulate mature B lymphocytes, but not T lymphocytes. The immune response mediated by such antigens only lasts for a short time, and cannot produce immunological memory. Since the immune function in infants under 2 years old is not well developed yet and has a poor response to T cell independent antigens, polysaccharide vaccines cannot induce an effective protective immune response in infants. Therefore, the 23-valent pneumococcal polysaccharide vaccine cannot be used in this high risk population.

7-valent pneumococcal polysaccharide-protein conjugate vaccine can prevent the diseases caused by 7 serotypes of *Streptococcus pneumoniae* covered by the vaccine. There are researches showing that the diseases caused by said 7 serotypes comprised therein account for about 80% of all pneumococcal diseases. In 2006-2007, in four typical children hospitals in China (i.e., Beijing Children Hospital, Children's Hospital of Fudan University, the Children's Hospital in Guangzhou and the Children's Hospital in Shenzhen), 279 strains of *Streptococcus pneumonia* were isolated in clinic from children with pneumonia under 5 years old, and it is found that the main serotypes of these clinical isolates are covered by PCV7, and said 7 serotypes account for about 81% of all the pathogenic pneumococcal strains. The results of the study demonstrated that the 7-valent pneumococcal conjugate vaccine has a relatively good serotype coverage in China. However, the 7-valent pneumococcal conjugate vaccine cannot prevent the infection caused by serotypes of *Streptococcus pneumoniae* other than said 7 serotypes, and there are researches showing that the infection by other serotypes of *Streptococcus pneumonia* also exists commonly and is rising.

Multiple membrane proteins on the cell surface of *Streptococcus pneumonia* are important virulence factors, and can also be important antigens. Since many outer membrane proteins have conservative constitutive structures among different serotypes of *Streptococcus pneumonia*, they can therefore induce cross immune protection. Pneumococcal surface protein A (PspA) is widely present in more than 90 subtypes of *Streptococcus pneumonia*. The α-helical terminus of the PspA protein is an important antigen determinant region and is highly conservative in different serotypes. Depending on the terminal amino acid sequence, the PspA proteins can be divided into three families, and further divided into six clades.

There are a lot of researches reporting that immunization with the PspA protein is protective against different serotypes of S.pn, and inclusion of the PspA protein as a vaccine component can overcome the shortcomings associated with the polysaccharide-protein conjugate vaccines, which only generate protections against a limited number of capsular serotypes and antibodies raised against the protein carrier lack specific protection against pathogenic bacteria. Epidemiological investigation shows that the PspA proteins from almost all pneumococcal strains isolated in clinic belong to family I and II, and the strains with the PspA proteins belonging to family III are rarely isolated.

Pneumolysin (Ply) mainly plays a role in hemolysis and complement activation Immunization of mice with the recombinant Ply, followed by challenging of *Streptococcus pneumonia* in nasal cavity and peritoneal cavity, demonstrate that Ply can prolong the life span of mice by 89% and 93%. The amino acid sequences of Ply are highly conservative and the protein is highly immunogenic. Therefore, Ply has been studied in different labs as a vaccine candidate which may potentially cover all the serotypes.

Although PspA and Ply have been shown to be good vaccine candidates, it is not clear yet how the proteins will interact with each other when both are present in the same formulation. In addition, PspA proteins are divided into several families and clads, and it is generally accepted that two or three PspA proteins from family I and II should be included in the vaccine formulation. In order to prepare a vaccine with a wide coverage and efficient protection against pneumococcal infections, it is of great significance to screen out protein immunogenic compositions involving multiple PspA proteins as well as the Ply protein.

Therefore, the invention provides an immunogenic composition, which will cover more than 95% of the serotypes isolated in clinic, when the immunogenic composition is used as antigen component.

CONTENTS OF INVENTION

One object of the invention is to provide an immunogenic composition for preventing pneumococcal diseases, and a vaccine formulation or a kit comprising the composition. The inventors surprisingly found that the immunogenic composition can prevent infection and invasion by *Streptococcus pneumonia*, covering more than 95% of serotypes.

Another object of the invention is to provide a method for preparing the immunogenic composition for preventing infectious diseases caused by *Streptococcus pneumonia*.

In order to fulfill said objects, in one aspect, the invention provides an immunogenic composition for preventing pneumococcal diseases, comprising pneumoly sin and at least two pneumococcal surface protein A.

Preferably, the pneumococcal surface protein A is selected from PspA-mRX1 (RX1 subtype pneumococcal surface protein A with its homology to human myosin reduced), PspA-EF5668 (EF5668 subtype pneumococcal surface protein A), and PspA-EF3296 (EF3296 subtype pneumococcal surface protein A).

Preferably, the pneumolysin is selected from PlyL460D, i.e., a modified pneumolysin.

Preferably, the immunogenic composition for preventing pneumococcal diseases according to the invention comprises PspA-mRX1, PspA-EF5668, PspA-EF3296 and PlyL460D.

In the immunogenic composition according to invention, PspA-mRX1 is from PspA family I, PspA-EF5668 and PspA-EF3296 are from PspA family II. Pneumolysin mainly plays a role in hemolysis and complement activation. The *Streptococcus pneumonia* challenge experiments in nasal cavity and peritoneal cavity demonstrate that the recombinant Ply can prolong the life span of mice by 89% and 93%. The amino acid sequences of Ply are highly conservative, and have a strong antigenicity. Therefore, Ply can be used as a candidate protein for an antigen vaccine covering almost all the serotypes, and the potential of the protein as a vaccine candidate has been demonstrated in different labs.

In the embodiments of the invention, the sequence of PspA-mRX1 has an identity of above 80%, preferably above 85%, 90%, 95% or 98%, to the sequence set forth in SEQ ID NO: 1 in the sequence listing, and more preferably, its sequence is the sequence set forth in SEQ ID NO: 1. The sequence of PspA-EF5668 has an identity of above 80%, preferably above 85%, 90%, 95% or 98%, to the sequence set forth in SEQ ID NO: 2 in the sequence listing, and more preferably, its sequence is the sequence set forth in SEQ ID NO: 2. The sequence of PspA-EF3296 has an identity of above 80%, preferably above 85%, 90%, 95% or 98%, to the sequence set forth in SEQ ID NO: 3 in the sequence listing, and more preferably, its sequence is the sequence set forth in SEQ ID NO: 3. The sequence of PlyL460D has an identity of above 80%, preferably above 85%, 90%, 95% or 98%, to the sequence set forth in SEQ ID NO: 4 in the sequence listing, and more preferably, its sequence is the sequence set forth in SEQ ID NO: 4.

Preferably, each of PspA-mRX1, PspA-EF5668, PspA-EF3296 and PlyL460D is present in an amount of 10-100 µg/mL, i.e., the dosages of the components in the immunogenic composition are as follows:

(1) the amount of PspA-mRX1 is 10-100 µg/mL;
(2) the amount of PspA-EF5668 is 10-100 µg/mL;
(3) the amount of PspA-EF3296 is 10-100 µg/mL; and
(4) the amount of PlyL460D is 10-100 µg/mL.

Preferably, in the immunogenic composition for preventing pneumococcal diseases, the mass ratio of PspA-mRX1, PspA-EF5668, PspA-EF3296 and PlyL460D is 1:1:1:1.

Preferably, in the immunogenic composition for preventing pneumococcal diseases, the PspA-mRX1 is prepared according to the invention patent with an application number of 201110455047.3.

Preferably, the immunogenic composition further comprises an adjuvant, wherein the adjuvant is in a concentration of 0.4-0.6 mg/mL, preferably 0.48 mg/mL. Preferably, the adjuvant includes aluminum adjuvant such as aluminum hydroxide or aluminum sulfate.

In the particular embodiments of the invention, the immunogenic composition further comprises a diluent, wherein the diluent is selected from one or more of physiological saline, phosphate buffer, Tris buffer, borate buffer, succinate buffer, histidine buffer, PBS buffer or citrate buffer; and is preferably physiological saline.

A person skilled in the art can know that a diluent can be present in a form premixed with each antigen stock solution, and the diluent components containing each antigen stock solution are mixed with each other prior to clinical application (e.g., by virtue of syringe); the diluent may also be present in an independent form, and prior to clinical application, each antigen stock solution is in contact with the diluent at the same time or sequentially, and the resulting mixture is mixed homogeneously.

The invention also provides a vaccine formulation for preventing pneumococcal diseases, comprising the immunogenic composition according to the invention.

Furthermore, the invention provides a kit for preventing pneumococcal diseases, comprising the immunogenic composition according to the invention.

In the particular embodiments of the invention, the vaccine formulation/kit further comprises one or more pharmaceutically acceptable carriers and/or excipients, and is generally freeze-dried and stored.

In the particular embodiments of the invention, in the vaccine formulation/kit, the antigen components are separated from each other prior to use. For example, each antigen component is stored in a separate container or in a different chamber in a single container. More preferably, each antigen component may be stored in a sealed vial or a syringe; the vial may be made of glass, plastic materials, and the like, and the syringe may be a glass syringe, a plastic syringe, and the like. A person skilled in the art knows that a vial may have an opening that can be sealed with a rubber plug or a cap, so that the component in the vial can be conveniently taken out or a syringe can be inserted into the vial. The syringe can be provided with a needle, or can be used in combination with an independent needle. The syringe and the size of the needle can be selected by a person skilled in the art depending on practical need.

The dosage of the vaccine formulation according to the invention can be determined according to the technical standards (such as injection route, vaccination age) as well known in the art; preferably, each immunogenic component is present in an amount of 10~100 µg/mL, more preferably 30~70 µg/mL, most preferably 40-60 µg/mL, e.g., 50 µg/mL.

The vaccination routes for the vaccine formulation according to the invention include intradermal injection, subcutaneous injection, intramuscular injection, intraperitoneal injection and the like. Preferably, the immunogenic composition, the vaccine formulation or the kit according to the invention, is useful for preventing pneumococcal infection, preferably for preventing infection by the *Streptococcus pneumoniae* strains from PspA family I and II.

In addition, the invention also provides use of the immunogenic composition according to the invention in the manufacture of a vaccine formulation and a kit for preventing pneumococcal diseases.

The invention also provides a method for preparing the immunogenic composition for preventing pneumococcal diseases according to the invention, comprising the following steps of:

Preparing the antigen stock solutions for the immunogenic components, i.e., PspA-mRX1, PspA-EF5668, PspA-EF3296, and PlyL460D, in the formulation of the immunogenic composition of the invention, and mixing the antigen stock solutions with each other, wherein the components can be in contact with each other simultaneously or sequentially, and are finally mixed homogeneously; when they are mixed with each other sequentially, the order is not defined.

Preferably, said four proteins PspA-mRX1, PspA-EF5668, PspA-EF3296 and PlyL460D have a final concentration of 10-100 μg/mL in the immunogenic composition.

In the preferred embodiments of the invention, the method comprises the following particular steps of:

(1) preparing the antigen stock solutions for the immunogenic components, i.e., PspA-mRX1, PspA-EF5668, PspA-EF3296, and PlyL460D, and aluminum adjuvant in the formulation of immunogenic composition of the invention, wherein based on the final concentration of 10-100 μg/mL for each of the four proteins of PspA-mRX1, PspA-EF5668, PspA-EF3296 and PlyL460D, and the final concentration of 0.4-0.6 mg/mL (preferably 0.48 mg/mL) for aluminum ion, the amounts of the antigen stock solutions, the adjuvant and the supplemented physiological saline are calculated;

(2) to the calculated amount of physiological saline, adding a corresponding amount of aluminum adjuvant, mixing them homogeneously; and adding the four antigen stock solutions PspA-mRX1, PspA-EF5668, PspA-EF3296 and PlyL460D, mixing them upside down, and storing them at 2-8° C. overnight to obtain the immunogenic composition.

The beneficial effects of the invention are as follows.

The immunogenic composition for preventing pneumococcal diseases can prevent the infection and invasion by *Streptococcus pneumoniae* (PspA family I and II), covering more than 95% of serotypes, and the alterations of amino acids to the PspA-mRX1 antigen component can enhance the immunogenic efficacy exerted by the component in the immunogenic composition. The immunogenic composition can be widely applied in the prevention of pneumonia, and is suitable for large-scale production in industry for its simple preparation method, low production cost, and short production cycle.

EXAMPLES

Figure 1:
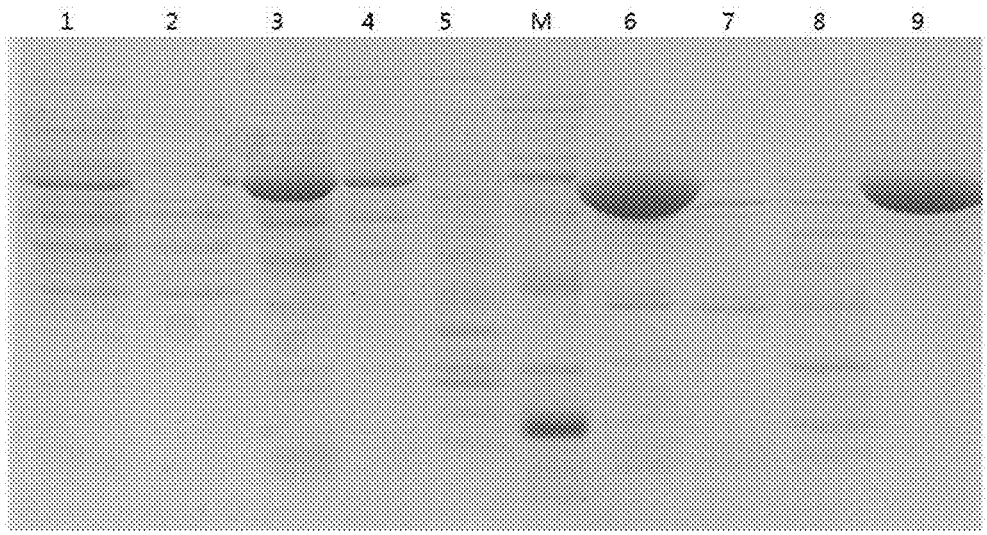
FIG. 1 is a SDS-PAGE electropherogram on purification of PspA-EF5668 antigen protein, wherein, 1: a disrupted solution: 2: SP flow through: 3: SP elution: 4: SP eluting tail: 5: column cleaning: 6: SP elution: 7: Q flow through: 8: impure protein elution: 9: target protein elution.

In the contents of the invention, the following terms have the meanings as described below.

The term "*Streptococcus pneumoniae* (*S. pn*)" is one of the most important pathogens causing serious invasive infection and upper respiratory tract infection, for example, is an important pathogenic bacterium for invasive and noninvasive infection such as pneumonia, meningitis, and otitis media. *Streptococcus pneumoniae* e is also one of the most important causes of death around the world. Generally, the bacterium resides in healthy human typically colonizing pharynx nasalis and may spread to lung to cause pneumonia when body's immune function weakens. One can also acquire pneumococcal infection by contacting other persons or patients who are infected by *Streptococcus pneumoniae*.

The term "PspA" refers to pneumococcal surface protein A (also called *Streptococcus pneumoniae* surface protein A), which is widely present in almost all subtypes of *Streptococcus pneumonia*. The α-Helical region of the N-terminus of the PspA protein is an important antigen determinant region, and is highly homologous among different serotypes. Depending on the terminal amino acid sequence, PspA proteins can be divided into three families, and further divided into six clades. Now, there are a lot of researches reporting that immunization with the PspA protein is protective against different serotypes of S.pn, and inclusion of PspA as a vaccine component can overcome the shortcomings that are associated with the polysaccharide-protein conjugate vaccines which can only prevent the infection by a limited number of capsular serotypes and antibodies raised against the protein carrier protein lack specific protection against pathogenic bacteria.

The term "PspA-mRX1" refers to RX1 subtype pneumococcal surface protein A with its homology to human myosin reduced, which belongs to PspA protein family I, and the sequence of which has an identity of above 80%, preferably above 85%, 90%, 95% or 98%, to the sequence set forth in SEQ ID NO: 1 in the sequence listing; and more preferably, is the sequence set forth in SEQ ID NO: 1.

The term "PspA-EF5668" refers to EF5668 subtype pneumococcal surface protein A, which belongs to PspA protein family II, and the sequence of which has an identity of above 80%, preferably above 85%, 90%, 95% or 98%, to the sequence set forth in SEQ ID NO: 2 in the sequence listing; and more preferably, is the sequence set forth in SEQ ID NO: 2.

The term "PspA-EF3296" refers to EF3296 subtype pneumococcal surface protein A, which belongs to PspA protein family II, and the sequence of which has an identity of above 80%, preferably above 85%, 90%, 95% or 98%, to the sequence set forth in SEQ ID NO: 3 in the sequence listing; and more preferably, is the sequence set forth in SEQ ID NO: 3.

The term "PlyL460D" refers to a modified *Streptococcus pneumoniae* (S.pn) Pneumolysin (Ply), the sequence of which has an identity of above 80%, preferably above 85%, 90%, 95% or 98%, to the sequence set forth in SEQ ID NO: 4 in the sequence listing; and more preferably, is the sequence set forth in SEQ ID NO: 4. Pneumolysin, which is one of the most important toxins of *Streptococcus pneumonia* and can dissolve the exotosin of erythrocytes, is present in almost all serotypes of *S. pn*, and is highly conservative. Now, it has been reported that Ply is expressed on surface of bacteria.

As used herein, the term "preventing/prevention" refers to the ability of avoiding, minimizing or making seizure or development of disease difficult by means of treatment, prior to seizure of disease.

As used herein, the terms "vaccine formulation", "kit", "diluent", "physiological saline", and "adjuvant" have the meanings as generally understood in the art.

The technical solutions of the invention are further described, but are not limited by the following examples.

Example 1

Preparation of Single Antigen Components

I. Construction of PspA-mRX1 was performed in accordance with the application with an application number of CN201110455047.3. The particular method was as followed.

Preparation of PspA-mRX1

*E. coli* BL21 (DE3) was used to express PspA-mRX1, and the particular method was as follows. The DNA fragment coding for the PspA protein of mRX1 was introduced into the plasmid pET9a, and the constructed plasmid was then introduced into *E. coli* BL21 (DE3) to obtain the strain for the expression of PspA-mRX1.

100 µL Cryopreserved bacterial seed of PspA-mRX1 *E. coli* BL21 (DE3) expression strain was pipetted and spread onto a plate, and cultured in a 37° C. incubator overnight. Bacterial lawn was scraped with a spreading rod and transferred to the medium in a 100 mL shake flask, cultured in a shaker at 37° C., 200-300 rpm for 3-4 h. A 50 L fermenter was inoculated with the culture from the shake flask and the bacteria were grown at 37° C., pH 7.0 with an agitation rate of 200-600 rpm. The feedings were added by a pH-star fed batch mode, and IPTG was added at the final concentration of 1 mM at one time in mid-log phase to induce the expression of the recombinant protein. After the culture, the fermentation broth was harvested and centrifuged to obtain bacterial cells. The cells were re-suspended and then disrupted by homogenization, and the supernatant was collected after centrifugation.

Purification of the PspA-mRX1 Antigen Protein

Citric acid solution was added to the supernatant at a ratio of 30-250 mL citric acid (1M) per 1 L disrupted solution. After stirring homogeneously, the resulting mixture was centrifuged and the supernatant was collected. The supernatant was first purified by SP FF: the column was equilibrated with citric acid buffer at pH of 3-4 and the protein was eluted with citric acid buffer at pH 5-6. The eluate from SP FF was then further purified by Q FF: the column was equilibrated with citric acid buffer at pH 7-8 and the target protein was eluted with citric acid buffer at pH 5-6. The purified PspA-mRX1 protein was analyzed (FIG. 1) and the purity was above 95%. The sequence of the PspA-mRX1 was as set forth in SEQ ID NO: 1 in the sequence listing.

II. Preparation of PspA-EF5668

*E. coli* BL21 (DE3) was used to express PspA-EF5668, and the particular method was as follows. The DNA fragment coding for PspA of EF5668 was introduced into the plasmid pET9a, and the constructed plasmid was then introduced into *E. coli* BL21 (DE3) to obtain the strain for the expression of PspA-EF5668.

100 µL Cryopreserved bacterial seed of the PspA-EF5668 *E. coli* BL21 (DE3) expression strain was pipetted and spread onto a plate, and cultured in a 37° C. incubator overnight. Bacterial lawn was scraped with a spreading rod and transferred to the medium in a 100 mL shake flask, cultured in a shaker at 37° C., 200-300 rpm for 3-4 h. A 50 L fermenter was inoculated with the culture from the shake flask and the cells were grown at 37° C., pH 7.0 with an agitation rate of 200-600 rpm. The feedings were added by a pH-star fed batch mode, and IPTG was added at the final concentration of 1 mM at one time in mid-log phase to induce the expression of the recombinant protein. After the culture, the fermentation broth was harvested and centrifuged to obtain the bacterial cells. The cells were re-suspended, and disrupted by homogenization, and the supernatant was collected after centrifugation.

Purification of the PspA-EF5668 Antigen Protein:

Citric acid solution was added at a ratio of 30-250 mL citric acid (1M) per 1 L disrupted solution. After stirring homogeneously, the resulting mixture was centrifuged and the supernatant was collected. The supernatant was first purified by SP FF: the column was equilibrated with citric acid buffer at pH of 3-4 and the protein was eluted with citric acid buffer at pH 5-6. The eluate was then purified by Q FF: the column was equilibrated with citric acid buffer at pH 7-8 and the target protein was eluted with citric acid buffer at pH 5-6. The purified PspA-EF5668 was analyzed (FIG. 1) and the purity was above 95%. The sequence of the PspA-EF5668 was as set forth in SEQ ID NO: 2 in the sequence listing.

III. Preparation of PspA-EF3296

The *E. coli* expression vector for the production of PspA-EF3296 was constructed by the same method. The particular method was as follows.

100 µL Cryopreserved bacterial seed of the EF3296 *E. coli* BL21 (DE3) expression strain was pipetted and spread onto a plate, and cultured in a 37° C. incubator overnight. Bacterial lawn was scraped with a spreading rod and transferred to the medium in a 100 mL shake flask, cultured in a shaker at 37° C., 200-300 rpm for 3-4 h. A 50 L fermenter was inoculated with the culture from the shake flask and the cells were grown at 37° C., pH 7.0, with an agitation rate of 200-600 rpm. The feedings were added by a pH-star fed batch mode, and IPTG was added at the final concentration of 1 mM at one time in mid-log phase to induce the expression of the recombinant protein. After the culture, the fermentation broth was harvested and centrifuged to obtain the bacterial cells. The cells were re-suspended and disrupted by homogenization, and the supernatant was collected after centrifugation.

Purification of the PspA-EF3296 Antigen Protein:

Citric acid solution was added at a ratio of 30-250 mL citric acid (1M) per 1 L disrupted solution. After stirring homogeneously, the resulting mixture was centrifuged and the supernatant was collected. The supernatant was purified first by SP FF: the column was equilibrated with citric acid buffer at pH of 3-4 and the protein was eluted with citric acid buffer at pH 5-6. The eluate was then further purified by Q FF: the column was equilibrated with citric acid buffer at pH 7-8 and the target protein was eluted with citric acid buffer at pH 5-6. The purified PspA-EF3296 was analyzed and the purity was above 95%. The sequence of the PspA-EF3296 was as set forth in SEQ ID NO: 3 in the sequence listing.

IV. Preparation of PlyL460D

*E. coli* BL21 (DE3) was used to express PlyL460D, and the particular method was as follows. 1004, Cryopreserved bacterial seed of the PlyL460D *E. coli* BL21 (DE3) expression strain was pipetted and spread onto a plate, and cultured in a 37 incubator overnight. Bacterial lawn was scraped with a spreading rod and transferred to the medium in a 100 mL shake flask, cultured in a shaker at 37° C., 200-300 rpm for 3-4 h. A 50 L fermenter was inoculated with the culture from the shake flask and the cells were grown at 37° C., pH 7.0, and with an agitation rate of 200-600 rpm. The feedings were added by a pH-star fed batch mode, and IPTG was added at the final concentration of 1 mM at one time in mid-log phase to induce the expression of the recombinant protein. After the culture, the fermentation broth was harvested and centrifuged to obtain bacterial cells. The cells were re-suspended and disrupted by homogenization, and the supernatant was collected after centrifugation.

Figure 2:
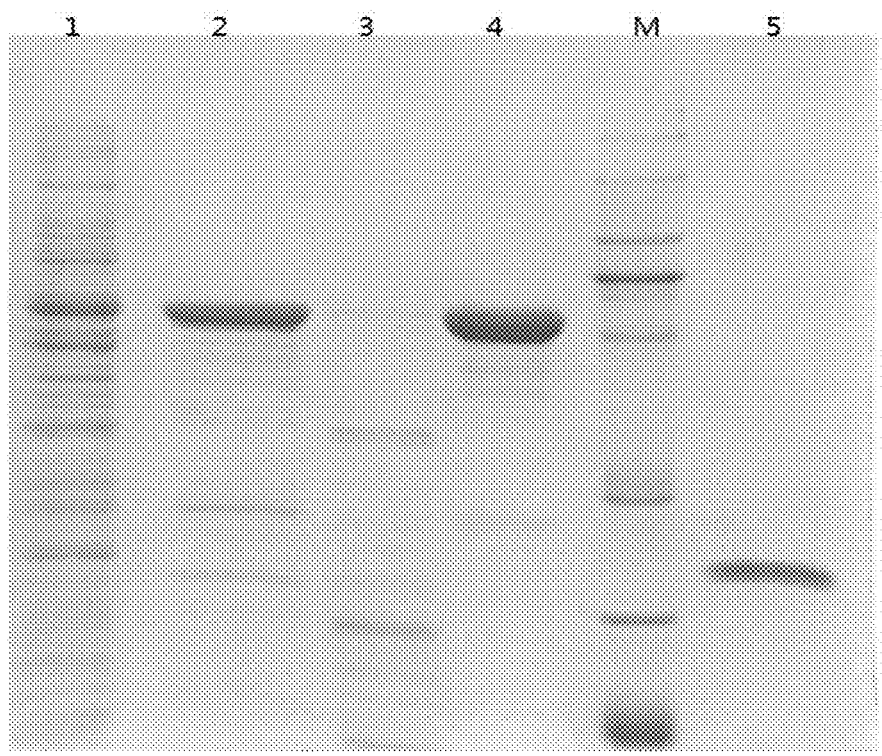
FIG. 2 is a SDS-PAGE electropherogram on purification of PlyL460D antigen protein, wherein, 1: a disrupted solution: 2: ammonium sulfate precipitation: 3: SP flow through: 4: elution: M: Marker: 5: column cleaning.

Purification of the PlyL460D Antigen Protein:

The cell lysate was treated by ultrafiltration using a 0.2 μm membrane, followed by medium exchanging and concentration using a 30 KD membrane. The target protein in the solution was first purified by Q 650 M: the column was equilibrated with Tris buffer, pH 8-9, and the protein was eluted with Tris buffer (pH 8-9) containing 50-250 mM NaCl. The eluate was then purified using a phenyl column: the column was equilibrated with Tris buffer (pH 8-9) containing 0.5-3M NaCl and the protein was eluted with Tris buffer at pH 8-9. The eluate was further purified by CHT I: the column was equilibrated with PB (4-10 mM) at pH 6.2, and the PlyL460D protein was eluted with PB (4-10 mM, pH 7-8) containing 0.5-1M NaCl. The result of the SDS-PAGE analysis of the purified PlyL460D protein was shown in FIG. 2. The sequence of the PlyL460D was as set forth in SEQ ID NO: 4 in the sequence listing.

Example 2

Preparation of the Formulations of Immunogenic Composition

The immunogenic compositions were prepared according to Table 1.

TABLE 1

| Composition name | Antigen component | | | |
|---|---|---|---|---|
| | PspA-EF5668 | PspA-EF3296 | PspA-mRX1 | PlyL460D |
| Composition 1 | 100 μg/mL | 100 μg/mL | 100 μg/mL | 100 μg/mL |
| Composition 2 | 50 μg/mL | 50 μg/mL | 50 μg/mL | 50 μg/mL |
| Composition 3 | 10 μg/mL | 10 μg/mL | 10 μg/mL | 10 μg/mL |

The preparation method was as follows.

(1) The antigen stock solutions and aluminum adjuvant in said formulation were prepared, wherein based on the final concentration of 100 μg/mL for each of the four proteins PspA-mRX1, PspA-EF5668, PspA-EF3296 and PlyL460D, and the final concentration of 0.48 mg/mL for aluminum ion, the amounts of the stock solutions, the adjuvant and the supplemented physiological saline were calculated.

(2) The materials needed for the preparation included physiological saline, pipette, transferpettor, pyrogen-free suction head, laboratory bottles, volumetric cylinder and the like, which were under ultraviolet radiation in a biosafety cabinet for 30 min prior to the preparation.

(3) Preparation of the formulations: in a biosafety cabinet, a volumetric cylinder was used to add the calculated amount of physiological saline to a laboratory bottle, and a pipette was used to add a corresponding amount of aluminum adjuvant; the resulting mixture was mixed homogeneously, and an equal volume of four stock solutions PspA-mRX1, PspA-EF5668, PspA-EF3296 and PlyL460D were added sequentially in this order; with the bottle cap screwed tightly, the bottle was shaken upside down, and placed at 2-8° C. overnight, to obtain the immunogenic composition 1.

(4) Except that the protein concentration was changed to 50 μg/mL in the step 1, the steps 1-3 were repeated to obtain the immunogenic composition 2; except that the protein concentration was changed to 10 μg/mL in the step 1, the steps 1-3 were repeated to obtain the immunogenic composition 3.

Example 3

Please refer to Example 2 for the method for preparing test samples.

The object of the experiment is to study a single antigen component for its protective efficacy in NIH mice infected with the WU2 strain or the Tigr4 strain of Streptococcus pneumoniae (determined by the survival rate of mice). 12-14 g NIH mice (10 mice per group) were subcutaneously injected with 10 μg/mL of a single antigen component (0.5 mL), or Al(OH)$_3$ as the control. Two boost vaccinations were carried out at a two-week interval. Prior to each immunization, blood samples were collected from the orbits. On day 45 (first immunization was performed on day 0), Streptococcus pneumoniae challenge was performed by intravenous injection (for the WU2 strain, 100 μl of the bacterial suspension containing 1.5×10$^7$ cells were injected to each mouse; for the Tigr4 strain, 100 μl of the bacterial suspension containing 1.0×10$^8$ cells were injected to each mouse), and the survival of the animals was monitored for 2 weeks.

Among said antigen components for preventing pneumococcal diseases, the PspA-mRX1 protein was found to be highly effective against challenge from the WU2 strain (PspA family I); the PspA-EF3296 and PspA-EF5668 both had a strong protection against challenge from the Tigr4 strain (PspA family II), but also had a good protection against challenge from the WU2 strain. The protection of the single component PlyL460D protein was not sufficient to produce a protective action against Streptococcus pneumoniae family. The results were shown in Table 2.

TABLE 2

Survival rate of the challenged mice (immunized with a single component antigen)

| challenge strain | Antigen component | | | | Control group |
|---|---|---|---|---|---|
| | PspA-EF5668 | PspA-EF3296 | PspA-mRX1 | PlyL460D | |
| WU2 | 60% | 60% | 100% | 30% | 10% |
| Tigr4 | 70% | 90% | 30% | 20% | 0 |

Example 4

Please refer to Example 2 for the method for preparing test samples.

The object of the experiment is to study a multivalent antigen composition for its protective efficacy in NIH mice infected with the WU2 strain or the Tigr4 strain (determined by the survival rate of mice). 12-14 g NIH mice (10 mice per group) were subcutaneously injected with a trivalent antigen composition or a tetravalent antigen composition at different antigen concentrations (injection volume 0.5 mL for each and Al(OH)$_3$ as control). Mice were immunized three times at a two week interval. Prior to each immunization, blood samples were collected from the orbit. On day 45 (first immunization was performed on day 0), Streptococcus pneumoniae challenge was performed by intravenous injection (for the WU2 strain, 100 µl of the bacterial suspension containing 1.5×10$^7$ cells were injected to each mouse; for the Tigr4 strain, 100 µl of the bacterial suspension containing 1.0×10$^8$ cells were injected to each mouse), and the survival of the animals was monitored for 2 weeks. The results on the protective efficacy were shown in Table 3.

TABLE 3

Survival rate of the challenged mice (immunized with multiple component antigens)

| Antigen components | Challenge strain | Amount of each antigen component (µg/mL) | | | |
|---|---|---|---|---|---|
| | | 10 | 2 | 0.4 | 0 |
| Tetravalent vaccine (EF5668 + EF3296 + RX1 + PLYL460D) | WU2 | 100% | 80% | 60% | 0 |
| | Tigr4 | 100% | 60% | 30% | 10% |
| Trivalent vaccine (EF5668 + EF3296 + RX1) | WU2 | 90% | 70% | 40% | 0 |
| | Tigr4 | 80% | 60% | 20% | 10% |

Note: the antigens were mixed at a ratio of PRX1:P3296:P5668: L460D=1:1:1:1.

The experimental results showed that, when the antigens were present in an amount of 10 µg/mL or 2 µg/mL in a tetravalent vaccine, the composition was highly protective against the WU2 strain and the Tigr4 strain. The protective efficacy was 100% against both strains at 10 µg/mL, and was 80% against the WU2 strain and 60% against the Tigr4 strain at 2 µg/mL.

As seen from the data in Tables 2 and 3, at the concentration of 10 µg/mL, the multivalent vaccine has a good protection against Streptococcus pneumoniae challenge of both the WU2 and Tigr4 strains. The protection efficacy of the multivalent vaccine was much better than any of the PspA antigen alone.

Although the trivalent PspA vaccine, containing PspA-mRX1, PspA-EF5668 and PspA-EF3296, was shown in the mouse model to be effective against Streptococcus pneumoniae challenge of both PspA family I and II strains, the tetravalent vaccine, including the 3 PspA components plus the PlyL460D protein, was found to offer a better and complete protection, indicating that the antigen PlyL460D can significantly enhance the immune response induced by the vaccine containing only three PspA antigens.

The PCT application of the present application is published in Chinese, and with subsequent entry into the national stage, there may be some differences due to the different languages in which the application is described, but these differences should not generate any influence on the scope of the present invention. For example, when the application is translated from Chinese to English, not matter specifically or not specifically indicated, differences such as singular or plural form, resulted from the translation, are within the scope of protection of the invention.

By reference to the Examples, the immunogenic composition for preventing pneumococcal diseases and the preparation method thereof are described in detail. However, it is for the purpose of describing rather than limiting the invention. Several examples can be listed within the defined scope, and therefore changes and modifications, made without departing from the general inventive concept of the invention, shall fall into the protection scope of the invention.

The invention claimed is:

1. An immunogenic composition for preventing pneumococcal diseases, characterized by comprising PspA-mRX1, PspA-EF5668, PspA-EF3296 and PlyL460D.

2. The immunogenic composition for preventing pneumococcal diseases according to claim 1, characterized in that each of the PspA-mRX1, PspA-EF5668, PspA-EF3296 and PlyL460D is present in an amount of 10-100 µg/mL.

3. The immunogenic composition for preventing pneumococcal diseases according to claim 2, characterized in that the mass ratio of PspA-mRX1, PspA-EF5668, PspA-EF3296 and PlyL460D is 1:1:1:1.

4. The immunogenic composition for preventing pneumococcal diseases according to claim 1, characterized in that the immunogenic composition further comprises a diluent and/or an adjuvant.

5. The immunogenic composition for preventing pneumococcal diseases according to claim 2, characterized in that the immunogenic composition further comprises a diluent and/or an adjuvant.

6. The immunogenic composition for preventing pneumococcal diseases according to claim 3, characterized in that the immunogenic composition further comprises a diluent and/or an adjuvant.

7. A vaccine formulation for preventing pneumococcal diseases, characterized in that the vaccine formulation comprises an immunogenic composition comprising PspA-mRX1, PspA-EF5668, PspA-EF3296 and PlyL460D.

* * * * *